(12) United States Patent
Magnenat et al.

(10) Patent No.: US 9,227,008 B2
(45) Date of Patent: Jan. 5, 2016

(54) PRESSURE MEASUREMENT UNIT FOR DETERMINING FLUID PRESSURE WITHIN A MEDICAL FLUID DISPENSING DEVICE

(71) Applicant: DEBIOTECH S.A., Lausanne (CH)

(72) Inventors: Olivier Magnenat, Lausanne (CH); Reto Cueni, Cugy (CH)

(73) Assignee: DEBIOTECH S.A., Lausanne (CH)

( * ) Notice: Subject to any disclaimer, the term of this patent is extended or adjusted under 35 U.S.C. 154(b) by 0 days.

(21) Appl. No.: 14/419,049

(22) PCT Filed: Jul. 25, 2013

(86) PCT No.: PCT/IB2013/056108
§ 371 (c)(1),
(2) Date: Feb. 2, 2015

(87) PCT Pub. No.: WO2014/020501
PCT Pub. Date: Feb. 6, 2014

(65) Prior Publication Data
US 2015/0217043 A1     Aug. 6, 2015

(30) Foreign Application Priority Data
Aug. 2, 2012 (EP) ........................................ 1217899

(51) Int. Cl.
*G01L 7/08* (2006.01)
*A61F 13/00* (2006.01)
(Continued)

(52) U.S. Cl.
CPC ................ *A61M 5/142* (2013.01); *G01L 19/00* (2013.01); *G01L 19/0023* (2013.01); *A61M 5/16854* (2013.01); *A61M 2205/12* (2013.01); *A61M 2205/3331* (2013.01)

(58) Field of Classification Search
None
See application file for complete search history.

(56) References Cited

U.S. PATENT DOCUMENTS 4,398,542 A * 8/1983 Cunningham .... A61M 5/16854
600/488
5,551,300 A * 9/1996 Vurek .................. A61B 5/0215
600/486
(Continued)

FOREIGN PATENT DOCUMENTS

EP          0 319 277        6/1989
WO    WO 2005/089832        9/2005
WO    WO 2007/085993        8/2007

OTHER PUBLICATIONS

International Search Report for PCT/IB2013/056108 mailed Oct. 7, 2013.
(Continued)

*Primary Examiner* — Peter Macchiarolo
*Assistant Examiner* — Jermaine Jenkins
(74) *Attorney, Agent, or Firm* — Nixon & Vanderhye P.C.

(57) ABSTRACT

A fluid container for a medical fluid dispensing device, comprises a rigid body (3) for delimiting with the inside part of its wall a volume of the medical fluid, and a membrane (5) that covers at least an opening of the rigid body thereby creating a fluid tight lid, the opening corresponding to a measurement area, and the membrane further covers a portion of an outside part of the rigid body's wall. The membrane comprises a flexible measurement part (11) corresponding to the opening of the rigid body, an attachment part (13) that is fixed to the rigid body, and a second part (12) that connects the flexible measurement part to the attachment part, and which comprises a rigid part (14), an upper part of which is connected to the flexible measurement part, and the rigid part further comprising a sealing surface (18), and a deformable part (15) which connects the rigid part to the attachment part. The fluid container further comprises a first gap (17) located between the rigid part and the rigid body, which is dimensioned to receive at least a part of the rigid part in a case when a force is applied onto the sealing surface and causes the deformable part to deform.

6 Claims, 6 Drawing Sheets

(51) Int. Cl.
*A61M 5/142* (2006.01)
*G01L 19/00* (2006.01)
*A61M 5/168* (2006.01)

(56) References Cited

U.S. PATENT DOCUMENTS

| | | | | |
|---|---|---|---|---|
| 5,614,677 | A | * | 3/1997 | Wamsiedler ........ A61M 1/3639 318/568.19 |
| 6,117,086 | A | * | 9/2000 | Shulze ................. A61B 5/0215 600/486 |
| 6,820,490 | B2 | * | 11/2004 | Mittelstein ............ G01L 9/0064 73/700 |
| 7,021,148 | B2 | * | 4/2006 | Kuhn .................. A61M 1/3639 73/714 |
| 8,104,352 | B2 | * | 1/2012 | Evering ................ A61M 5/145 73/706 |
| 2006/0226087 | A1 | | 10/2006 | Robinson et al. |

OTHER PUBLICATIONS

Written Opinion of the International Searching Authority mailed Oct. 7, 2013.

\* cited by examiner

PRESSURE MEASUREMENT UNIT FOR DETERMINING FLUID PRESSURE WITHIN A MEDICAL FLUID DISPENSING DEVICE

This application is the U.S. national phase of International Application No. PCT/IB2013/056108, filed 25 Jul. 2013 which designated the U.S. and claims priority to EP 12178990.3, filed 2 Aug. 2012, the entire contents of each of which are hereby incorporated by reference.

FIELD OF INVENTION

The present invention relates to pressure measurement of a fluid in a medical fluid dispensing device, for instance in a disposable fluid container.

STATE OF THE ART

In the medical field, injection of a substance to a patient prohibits any risk of contamination of the patient and so contamination of the liquid. A disposable set of fluid dispensing device and/or fluid container overcomes this risk but involves some other difficulties, particularly when the assessment of physical quantities is required. Indeed, the disposable set is designed for one use only and needs to be economically manufactured to reduce its cost. For control and monitoring purposes, it is desirable to measure the fluid pressure within the disposable set. However, this set cannot include any transducer which in general is too expensive. The disposable set requires one or more pressure transducers to be deported on the device and to find a coupling which allows to estimate physical quantities whereas the pressure transducer is not in direct contact with the fluid. In the case of pressure measurement, two cases may be differentiated:

the pressure is higher than a reference value (overpressure); or the pressure is lower than a reference value (depression).

In the case of overpressure, a flexible element (membrane) can simply be in contact with the pressure transducer (force or pressure). In the case of depression, it is necessary to add a fluid tight coupling around the membrane linking the pressure transducer to the disposable set.

The application WO 2007/085993 discloses a fluid pressure measuring unit for medical devices which traps an air volume between the pressure transducer's membrane and the disposable set's membrane. A sealing element which is slightly compressed ensures the fluid tightness of the system.

Several problems may be underlined:

Fluid Tightness

The pieces used—pressure transducer and disposable set—respect tolerances associated with their manufacturing process. In case we have several pressure measurements to perform at various places in the disposable set, the stack of tolerances can become important. It is then difficult to ensure the fluid tightness of all pressure transducers. In the application WO 2007/085993, the height of the sealing element is small; this implies that the fluid tightness is done with a little compression.

Preload

When coupling, the trapped air volume is slightly compressed and involves a deformation of the membrane in the disposable set while the pressure in the disposable set has not changed. This would have no effect on the measured value if the membrane in the disposable set could be considered as infinitely flexible. It is important to note that it is possible to play with the design of the membrane in order to increase its flexibility (thickness, diameter, corrugations). One of the solutions proposed in the application WO 2007/085993 is to add a valve which is piloted at a control interface.

Complexity

For reasons of thermal stability, it is imperative that the trapped air volume be the lowest possible. The solution proposed by the application WO 2007/085993 meets with difficulties of manufacture. It is very difficult to realize a channel that is small enough to avoid that the trapped volume increases.

The interface of a disposable set with a medical measurement device requires technical solutions which should be simple and reliable. Specifically for measurement purposes, the design must insure the functionality and controllability.

The current technical solutions are not able to fulfil all necessary requirements.

There is therefore a need to improve the pressure measurement of fluid in medical fluid dispensing devices and to ensure reliability and assembly repeatability.

GENERAL DESCRIPTION OF THE INVENTION

The above cited problem is solved with the present invention which provides in a first aspect a fluid container for a medical fluid dispensing device, comprising a rigid body for delimiting with the inside part of its wall a volume of the medical fluid, and a membrane that covers at least an opening of the rigid body thereby creating a fluid tight lid, the opening corresponding to a measurement area, and the membrane further covers a portion of an outside part of the rigid body's wall. The membrane comprises a flexible measurement part corresponding to the opening of the rigid body, an attachment part that is fixed to the rigid body, and a second part that connects the flexible measurement part to the attachment part, and which comprises a rigid part, an upper part of which is connected to the flexible measurement part, and the rigid part further comprising a sealing surface, and a deformable part which connects the rigid part to the attachment part. The fluid container further comprises a first gap located between the rigid part and the rigid body, which is dimensioned to receive at least a part of the rigid part in a case when a force is applied onto the sealing surface and causes the deformable part to deform.

In a second aspect the invention provides a fluid pressure measurement unit for measuring either positive or negative fluid pressure of a medical fluid in a fluid container, said unit comprising the fluid container according to the previous paragraph, and a pressure transducer comprising a planar measuring surface. The planar measuring surface is positioned against the sealing surface of the rigid part, thereby defining a fluid tight chamber that separates the membrane and the planar measuring surface, and the flexible measurement part is adapted to transmit pressure from the medical fluid to the pressure transducer.

In a first preferred embodiment of the fluid pressure measurement unit according to the invention, the rigid part is L-shaped, the upper part of the L being connected to the flexible measurement part, and the lower base part of the L offering the sealing surface.

In a second preferred embodiment of the fluid pressure measurement unit according to the invention, the deformable part is in a plane perpendicular to the flexible measurement part.

In a third preferred embodiment of the fluid pressure measuring unit according to the invention, the pressure transducer further comprises a sealing protrusion surrounding the planar measuring surface, whereby the sealing protrusion is positioned against the sealing surface of the rigid part, thereby defining the fluid tight chamber (9) that separates the membrane and the planar measuring surface.

In a fourth preferred embodiment of the fluid pressure measuring unit according to the invention, the sealing protrusion has an annular shape and extends vertically.

The present invention allows to perform a reliable coupling between transducer and disposable which
is insensible to the stack of tolerances of manufacture and assembly and
does not compress the air volume trapped between the transducer and the disposable.

It shows the following advantages:
very little air compression at the time of coupling between pressure transducer and disposable;
fluid tightness guaranteed by a good compliance of the system;
simplicity of the measurement device—pressure transducer—and the disposable set—fluid container;
no deformation of the flexible measurement part when a force is applied onto the sealing surface.

DETAILED DESCRIPTION OF THE INVENTION

The invention will be discussed below in a more detailed way with examples illustrated by the following figures.

NUMERICAL REFERENCES USED IN THE DRAWINGS

1. Fluid container
2. Pressure transducer
3. Rigid body
4. Medical fluid
5. membrane
6. Rigid cover plate
7. O-ring
8. Vertical sealing protrusion
9. Fluid tight chamber
10. Planar measuring surface
11. Flexible measurement part
12. Second part
13. Attachment part
14. Rigid part
15. Deformable part
16. Gap in rigid cover plate region
17. Gap in rigid body region
18. Sealing surface
19. Disposable set The invention is set forth and characterized in the independent claims, while the dependent claims describe other characteristics of the invention.

The present application claims the benefit of the priority of EP 12175498.0 filed on $2^{nd}$ august 2012 in the name of Debiotech, the entire disclosure of which is incorporated herein by reference.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used in this specification and the appended claims, the term "or" is generally employed in its sense including "and/or" unless the content clearly dictates otherwise.

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

Preferred Embodiment

Figure 1:
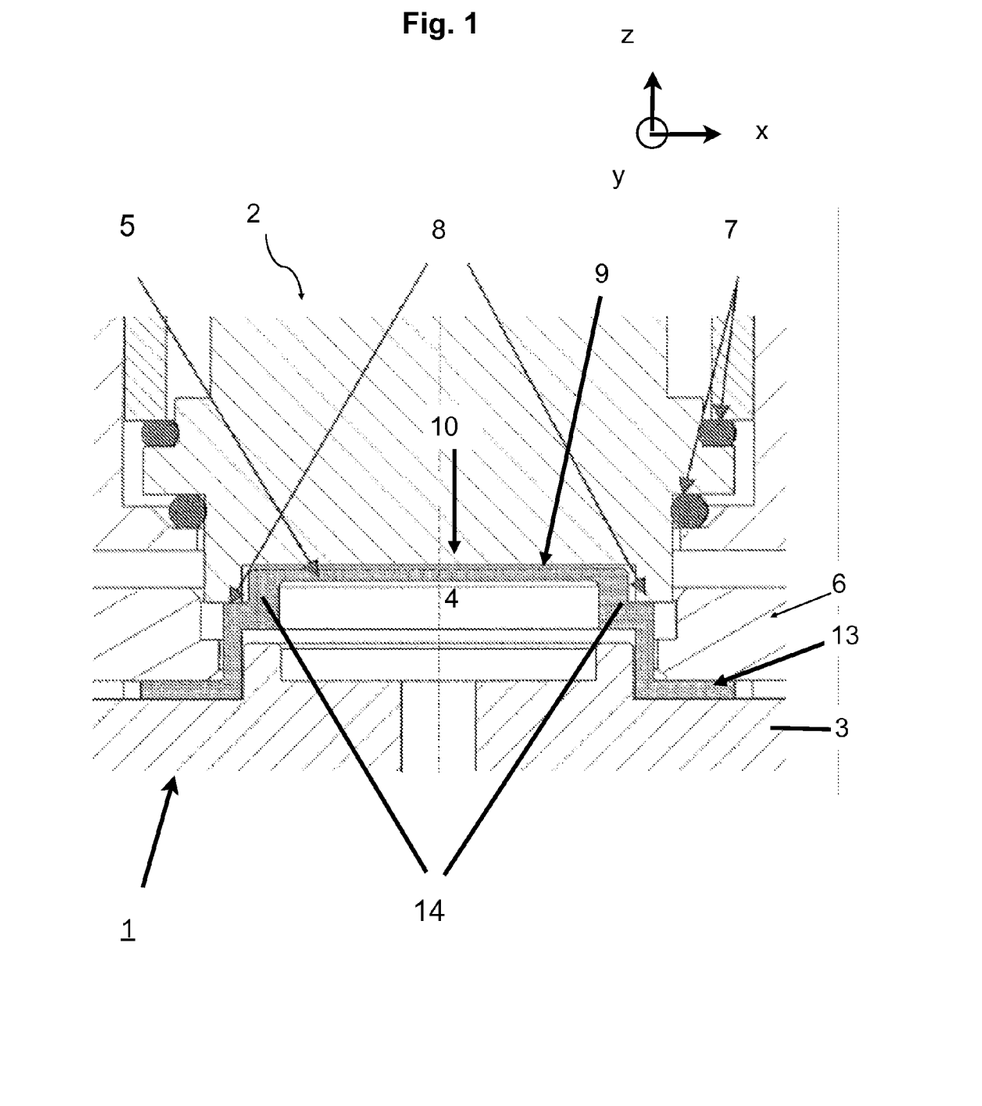
FIG. 1 shows an example embodiment of a fluid container according to the invention in a cross sectional view, with a coupling between the pressure transducer and the fluid container of the disposable set. The view is drawn in the usual mechanical norm, according to which hatched surfaces represent parts that are in the plane of the drawing.

Referring to FIG. 1, the description below presents an example solution as a preferred embodiment to couple a pressure transducer 2 with a fluid container 1 of a disposable set, which is covered by a membrane 5.

Figure 5:
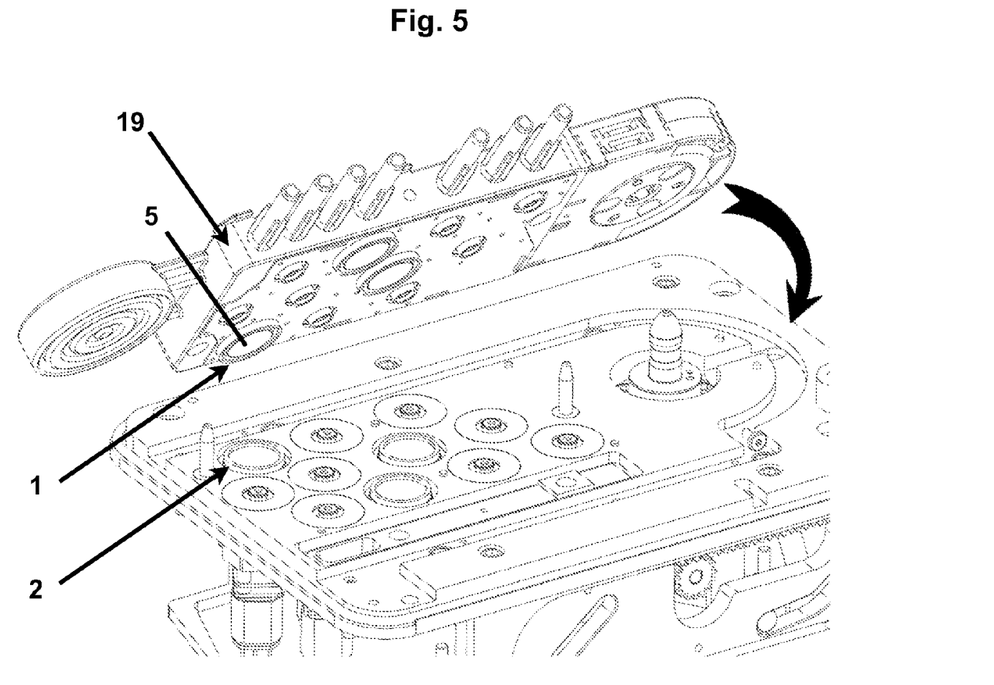
FIG. 5 shows an example of a disposable set and a counterpart assembly carrying at least one pressure transducer.

Referring to FIG. 5, this shows an example embodiment of a disposable set 19 and a counterpart assembly carrying at least one pressure transducer 2. The disposable set 19 comprises at least one fluid container 1 corresponding to the at least one pressure transducer 2, the former which is covered by the membrane 5

As shown on FIG. 1, the fluid container 1 is connected to a medical measurement device (not shown), which is equipped with the pressure transducer 2.

The fluid container 1 comprises:
a rigid body 3 defining a volume for a medical fluid 4, the pressure of which is to be measured;
the membrane 5 which is used as a flexible tight barrier between the medical fluid 4 and the pressure transducer 2;
a rigid cover plate 6 to maintain the membrane 5 outside of the measurement area.

It is to be noted that the rigid cover plate 6 is an optional feature of the fluid container 1. As such it may well be omitted and/or replaced by other means.

A planar measuring surface 10 of the medical device (illustrated only partially in the figure) is equipped with the pressure transducer 2. A housing of the pressure transducer 2 rests on O-rings 7. The O-rings 7 are elastic elements that allow the pressure transducer 2 to be moved and thus imply that the positioning of the pressure transducer 2 may be adapted relative to the fluid container 1's positioning firstly in a plane of the planar measuring surface 10 (herein the plane is defined by x-y axises, illustrated in FIG. 1 by a coordinate system, whereby the y-axis is perpendicular to the plane of the paper on which the figure is drawn) and secondly in an angle of inclination defined with respect to the planar measuring surface 10 (called θ-angle in the following).

Additionally, the pressure transducer 2 comprises a vertical—along the z-axis—sealing protrusion 8 of annular shape. The vertical sealing protrusion 8 may be pressed during instrument coupling against a surface of a rigid part 14 of the membrane 5. The instrument coupling creates a fluid tight air chamber 9 between the planar measuring surface 10 of the pressure transducer 2, and the membrane 5.

Figure 2:
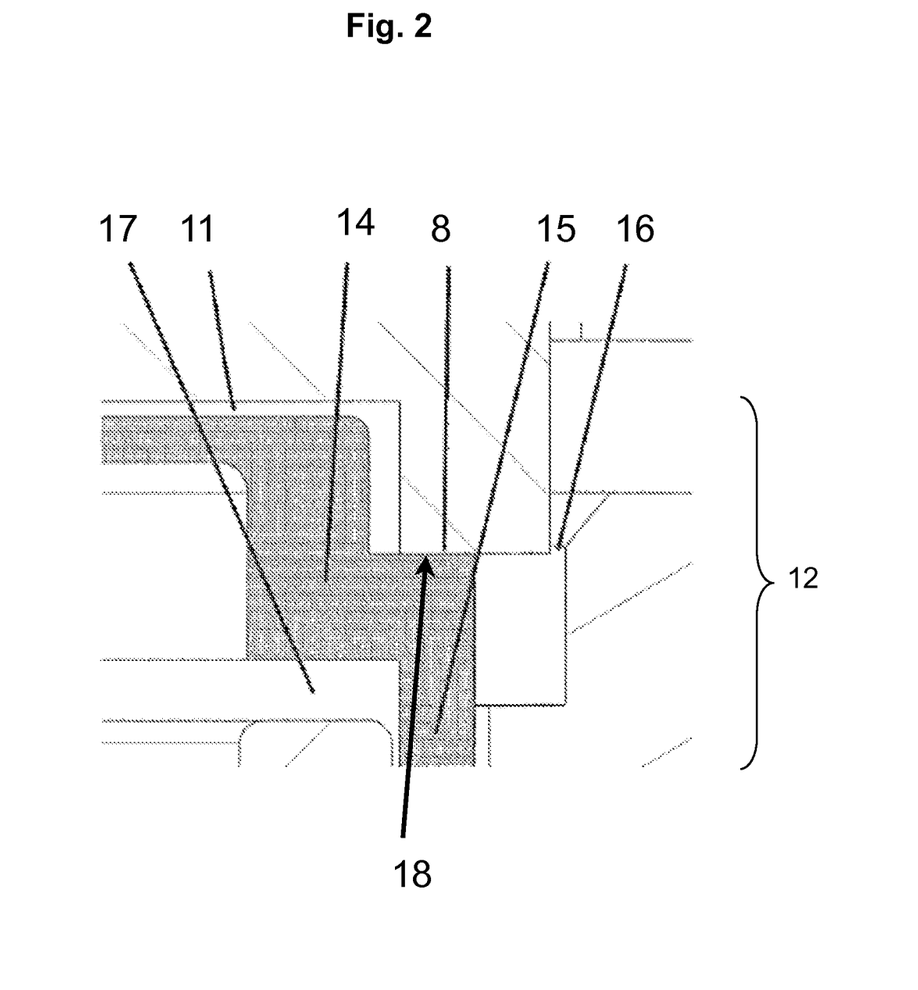
FIG. 2 shows an enlarged view of the coupling according to the example embodiment of the invention.

As shown in FIG. 2, the membrane 5 comprises a flexible measurement part 11 adapted to transmit pressure from the fluid container 1 to the pressure transducer 2, a second part 12 which is a ring and an attachment part 13 (only shown in FIG. 1) which may be in a plane parallel to the flexible measurement part 11. Said flexible measurement part 11 may be circular shape and may have a diameter comprised between 0 to 50 mm, advantageously between 8 to 17 mm. The second part 12 comprises the rigid part 14, a sealing surface 18 and a deformable part 15 which may be reversibly and elastically deformed. The sealing surface 18 is intended to enter in contact with the vertical sealing protrusion 8. In one embodiment, the deformable part 15 may be at least partially aligned with the vertical sealing protrusion 8 and both may have the same direction (parallel to the Z-axis).

The membrane 5 may be made of silicone or other soft material. The rigid part 14 may be made of silicone, other soft material or other material which is not or less soft.

Figure 6:
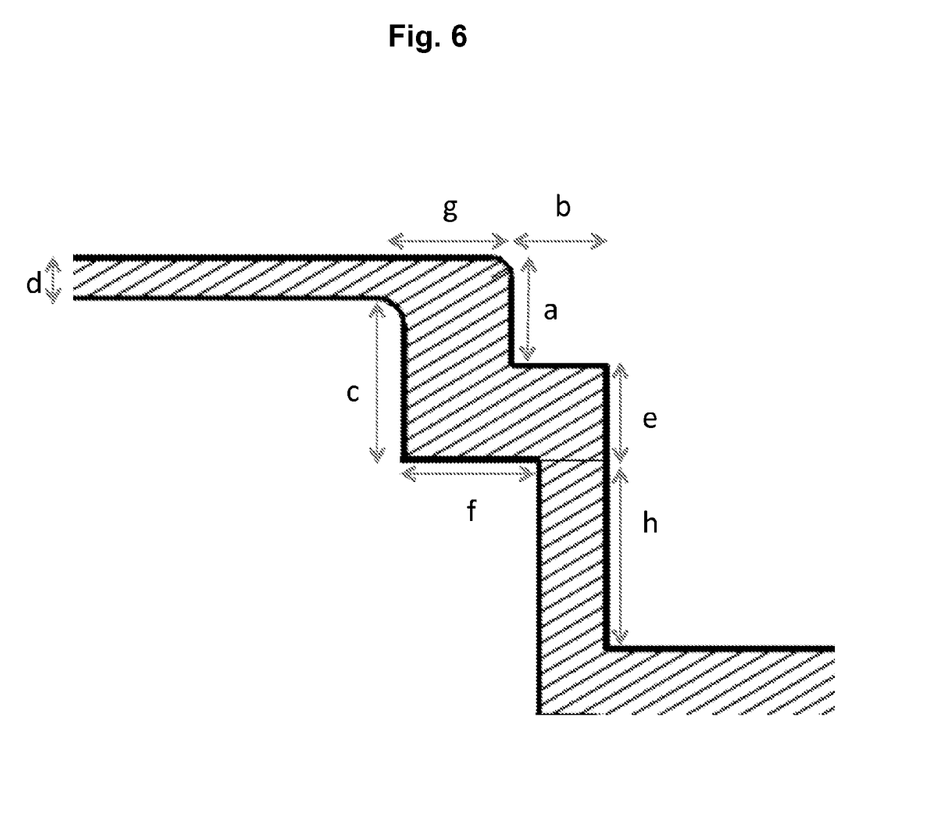
FIG. 6 shows a part of the membrane and the reference "a" to "h"

In a preferred embodiment, the rigid part 14 of the membrane 5 may be in the form of an L. Referring to FIG. 6, the dimensions of different parts are named according the references "a" to "h". Said references are examples and may vary. The reference "a" may be comprised between 0 to 5 mm, advantageously between 0.5 to 1 mm. The reference "b" may be comprised between 0 to 5 mm, advantageously between 0.5 to 1 mm. The reference "c" may be comprised between 0 to 10 mm, advantageously between 0.5 to 2 mm. The reference "d" may be comprised between 0 to 5 mm, advantageously between 0.1 to 0.5 mm. The reference "e" may be comprised between 0 to 5 mm, advantageously between 0.5 to 1 mm. The reference "f" may be comprised between 0 to 10 mm, advantageously between 0.5 to 3 mm. The reference "g" may be comprised between 0 to 5 mm, advantageously between 0.5 to 1 mm. The reference "h" may be comprised between 0 to 10 mm, advantageously between 0.5 to 5 mm.

In case of the rigid part 14 is in the form of an L, the height of sealing protrusion 8 must be at least equal than the reference "a" shown in FIG. 6. If said height is equal to "a", then the fluid tight chamber 9 is equal to 0. In a preferred embodiment, the fluid tight chamber 9 is as small as possible, thus the height of sealing protrusion 8 must be a slightly greater than "a".

The rigid part 14 is rigid compared to the more flexible measurement part 11, the attachment part 13 and deformable part 15 of the membrane 5. The rigidness of rigid part 14 may be achieved by varying the thickness of the material used to produce the rigid part 14, and make sure that the thickness is relatively larger than that of other constituents of the second part 12 and/or than the flexible measurement part 11. The rigidness of the rigid part 14 is required to maintain the overall inside volume of the fluid container 1. Thus, when a force is applied onto the sealing surface 8, the rigidness and/or the design of the rigid part 14 allows the deformable part 15 to deform while the flexible measurement part 11 not to deform. Thus, only the pressure of the fluid deforms the flexible measurement part 11.

A gap in the rigid body 3 has the reference 17 and may be realised as a space between the lower part of the rigid part 14 and the rigid body 3 that allows a movement of the rigid part 14 and the flexible measurement part 11 according to the z-axis, which is perpendicular to the earlier defined x-y-axis-plane (see FIG. 1). The movement of the rigid part 14 and the flexible measurement part 11 according to the z-axis is rendered possible also through the feature that the deformable part 15 is deformable in the z-axis direction. Said gap 17 may be inside of and/or is a part of the volume of the fluid container 1.

In one embodiment, to ensure that a correct positioning is achieved after the coupling of fluid container 1 and pressure transducer 2, a further gap exists in the rigid cover plate 6 region. The gap in the rigid cover plate 6 region has the reference 16 and may be realised as a bore that allows guiding the pressure transducer 2 during the coupling.

As has already been mentioned herein above, the rigid cover plate 6 is an optional feature. The membrane 5 may well be fixed to the rigid body 3 by any other means, whereby such any other means could for example apply to the attachment part 13.

General Principle of Fluid Container

Figure 3:
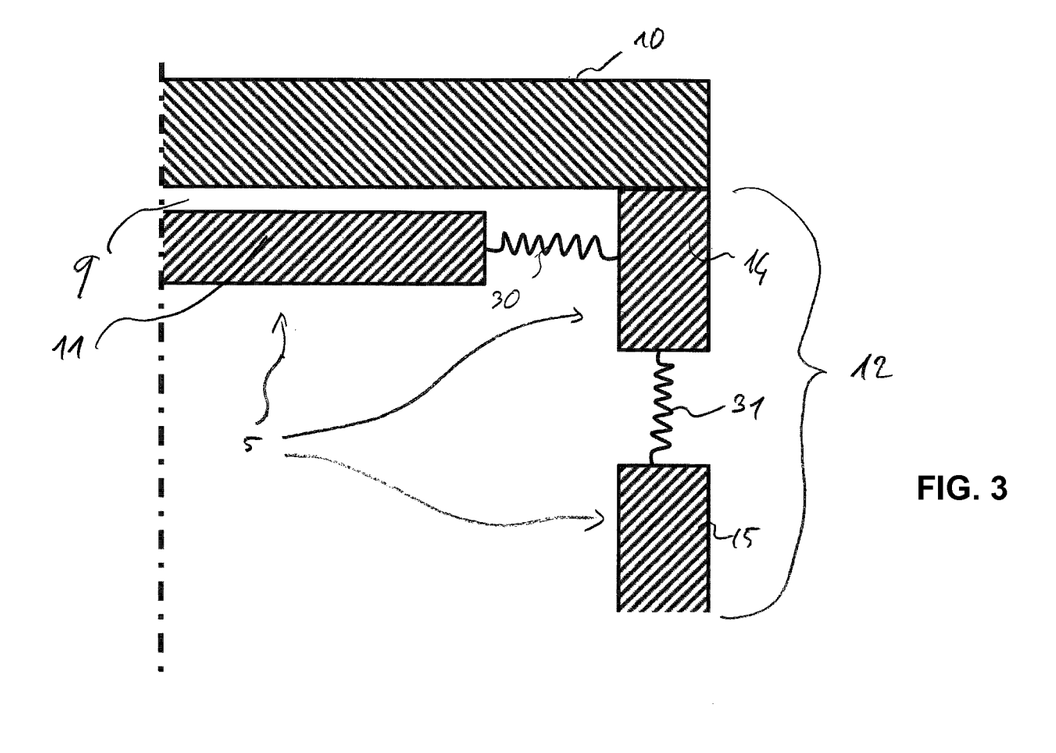
FIG. 3 contains a schematic representation of a detail of a coupling according to the invention.

FIG. 3 contains a schematic representation of the membrane 5 and its second part 12. FIG. 3 aims at providing a generic explanation that allows a person skilled in the art to reproduce the invention without being tied to the specific preferred embodiment shown in FIGS. 1 and 2.

The membrane 5 comprises the flexible measurement part 11. While in FIG. 2 the property of flexible measurement part 11 to be flexible, i.e., to allow to deform in order to transmit pressure from the fluid container to the pressure transducer, may be achieved by choosing the thickness of the flexible measurement part 11 sufficiently thin to remain elastic to this purpose, in FIG. 3, the flexibility is represented by a first spring 30. The latter first spring 30 allows the flexible measurement part 11 to remain movable with respect to the rigid part 14, to an extent allowed by the first spring's mechanical properties.

The membrane 5 further comprises the deformable part 15. While in FIG. 2 the property of the deformable part 15 to be deformable, i.e., to allow deforming in order to position the planar measuring surface 10 relative to the fluid container, may be achieved by choosing the thickness of the deformable part 15 sufficiently thin to remain elastic to this purpose, in FIG. 3, the deformability is represented by a second spring 31. The latter second spring 31 allows the deformable part 15 to remain movable with respect to the rigid part 14, to an extent allowed by the second spring's mechanical properties.

It is to be noted that the schematic representation of FIG. 3 makes it clear that the vertical sealing protrusion 8 as shown in FIGS. 1 and 2 is in fact an optional feature that can well be omitted when realising the invention.

Figure 4:
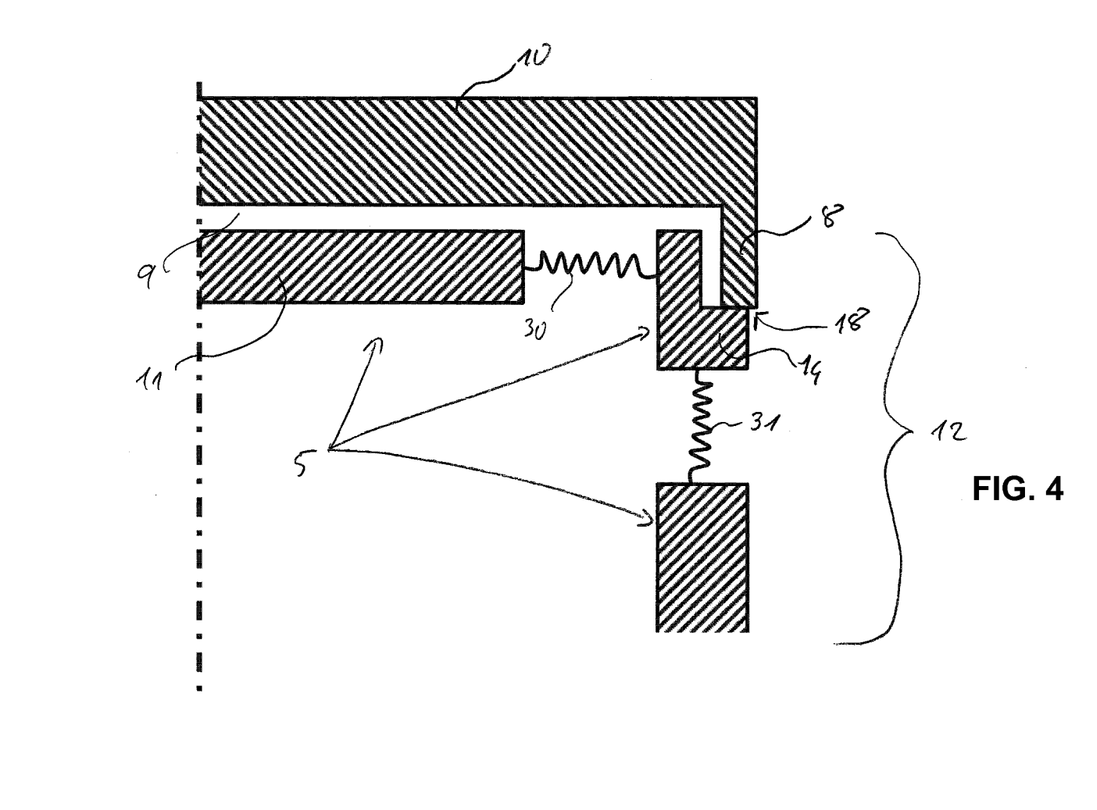
FIG. 4 contains a further schematic representation of a detail of a coupling according to yet an other example of the invention.

FIG. 4 contains a schematic representation of the membrane 5 and its second part 12, wherein the planar measuring surface 10 comprises the vertical sealing protrusion 8, which has a similar function as in FIGS. 1 and 2. While the assembly in FIG. 4 may mostly be described in a similar manner as for FIG. 3, it is shown in addition that the second part 12 comprises the sealing surface 18 which is intended to enter in contact with the vertical sealing protrusion 8, when the planar measuring surface 10 is positioned in proximity of the fluid container.

How the Coupling Works

The fluid container 1 is disposed face to face with the pressure transducer 2 of the medical device (not shown in the figures).

The fluid container 1 is displaced according to the z-axis. The pressure transducer 2 is guided by the gap in the rigid cover plate region 16 in order to ensure that a surface of the vertical sealing protrusion 8 enters in contact with the sealing surface 18 of the rigid part 14 in the second part 12.

Then the pressure transducer 2 with the vertical sealing protrusion 8 continues to be moved towards the sealing surface 18. The deformable part 15 of the second part 12 is compressed and deformed according to the z-axis. This deformable part 15 of the second part 12 exerts a back-moving force which ensures the fluid tight sealing. The rigid part 14 of the second part 12 does not lose its shape under the force applied by the vertical sealing protrusion 8 and simply follows it. The rigid part and/or the flexible measurement part 11 move to the fluid which is contained in the fluid container 1.

The assembly allows ensuring the reliability of the coupling between the pressure transducer 2 and the membrane 5 for an important range of transducer positions and this without compressing the volume of the air trapped in the fluid tight chamber 9.

The design of the membrane 5 will adapt to the transducer's geometry, for example, if the transducer has a flange or not, if the transducer membrane is plane, rounded or with corrugations.

The invention claimed is:

1. A fluid container for a medical fluid dispensing device, comprising
   a rigid body for delimiting with the inside part of its wall a volume of the medical fluid;
   a membrane that covers at least an opening of the rigid body thereby creating a fluid tight lid, the opening corresponding to a measurement area, and the membrane further covers a portion of an outside part of the rigid body's wall;
   wherein the membrane comprises
      a flexible measurement part corresponding to the opening of the rigid body;
      an attachment part that is fixed to the rigid body;
      a second part that connects the flexible measurement part to the attachment part, and which comprises
         a rigid part, an upper part of which is connected to the flexible measurement part, and the rigid part further comprising a sealing surface; and
         a deformable part which connects the rigid part to the attachment part,
   and the fluid container further comprising:
      a first gap located between the rigid part and the rigid body, which is dimensioned to receive at least a part of the rigid part in a case when a force is applied onto the sealing surface and causes the deformable part to deform.

2. A fluid pressure measurement unit for measuring either positive or negative fluid pressure of a medical fluid in a fluid container, said unit comprising:
   the fluid container according to claim 1,
   a pressure transducer comprising:
      a planar measuring surface,
   wherein
      the planar measuring surface is positioned against the sealing surface of the rigid part, thereby defining a fluid tight chamber that separates the membrane and the planar measuring surface, and
      the flexible measurement part is adapted to transmit pressure from the medical fluid to the pressure transducer.

3. The fluid pressure measurement unit according to claim 2 wherein the rigid part is L-shaped, the upper part of the L being connected to the flexible measurement part, and the lower base part of the L offering the sealing surface.

4. The fluid pressure measurement unit according to claim 2 wherein the deformable part is in a plane perpendicular to the flexible measurement part.

5. The fluid pressure measuring unit according to claim 2 wherein the pressure transducer further comprises a sealing protrusion surrounding the planar measuring surface,
   whereby
      the sealing protrusion is positioned against the sealing surface of the rigid part, thereby defining the fluid tight chamber that separates the membrane and the planar measuring surface.

6. The fluid pressure measuring unit according to claim 5, wherein the sealing protrusion has an annular shape and extends vertically.

* * * * *